United States Patent [19]

Hazar

[11] 4,097,992
[45] Jul. 4, 1978

[54] METHOD FOR PRODUCING ARTIFICIAL DENTURES

[75] Inventor: Mitchell M. Hazar, Phoenix, Ariz.

[73] Assignee: Warner-Lambert Company, Morris Plains, N.J.

[21] Appl. No.: 726,812

[22] Filed: Sep. 27, 1976

[51] Int. Cl.² .............................................. A61G 13/00
[52] U.S. Cl. ................................................................ 32/2
[58] Field of Search ........................................ 32/2, 11

[56] References Cited

U.S. PATENT DOCUMENTS

| 3,460,252 | 8/1969 | Schneider et al. | 32/2 |
| 3,567,806 | 3/1971 | Dyal | 32/2 |
| 3,839,796 | 10/1974 | Hazar | 32/2 |
| 4,012,838 | 3/1977 | Abdenour | 32/2 |
| 4,017,971 | 4/1977 | Hazar | 32/2 |

Primary Examiner—Louis G. Mancene
Assistant Examiner—John J. Wilson
Attorney, Agent, or Firm—John A. Robertson; Don J. Flickinger

[57] ABSTRACT

The disclosure relates to a method for producing artificial dentures comprising the preparation of a plurality of substantially identical generally U-shaped hard base denture elements and fixing teeth thereto and using one of the hard base elements with teeth thereon to produce a temporary denture with a soft layer thereon and formably fitting the soft layer to a patient's mouth; then placing impression formable material in the soft layer and inserting it in the patient's mouth to impression form the impression formable material so as to attain a model upon which dental stone molds are cast; then placing another one of said substantially identical hard bases with teeth attached thereto in one of the dental stone molds and subsequently casting a hard impressionable plastic material against the opposite side of said denture element from said teeth and allowing the last mentioned material to cure and bond to the said substantially identical hard base element to thereby form a hard structural denture which conforms to the patient to which the aforementioned formable layer was impression fitted by the first mentioned impression formable material.

The disclosure also relates to a rubber-like shield which may be placed over the generally U-shaped hard base denture element and the teeth fixed thereto such that portions of the teeth and the opposite portion of the hard base are exposed and whereby the shield prevents dental stone from adhering to the teeth and the U-shaped base during the casting of the dental stone molds therearound and subsequently during the final casting of the final impression formable material in the molds against the U-shaped base opposite to the teeth fixed thereon.

3 Claims, 8 Drawing Figures

U.S. Patent  July 4, 1978  Sheet 2 of 2  4,097,992
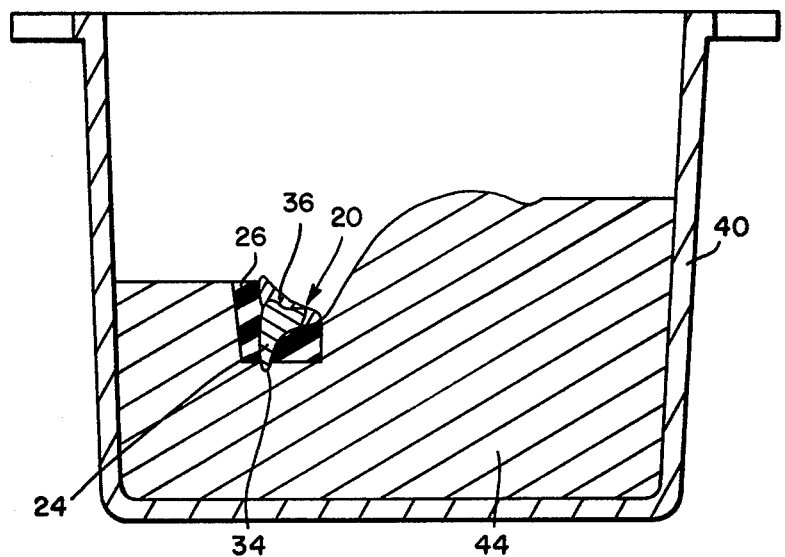
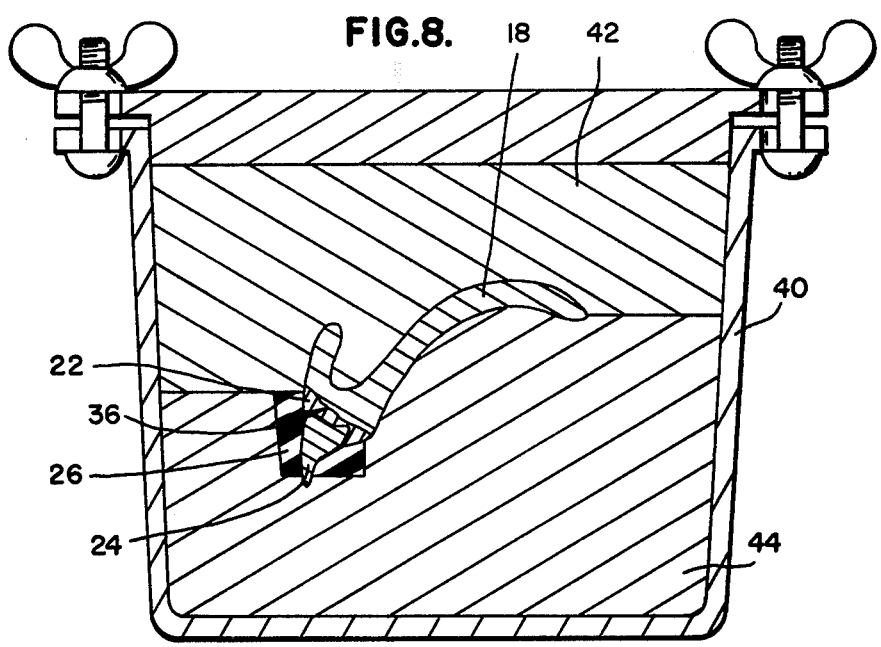

METHOD FOR PRODUCING ARTIFICIAL DENTURES

BACKGROUND OF THE INVENTION

U.S. Pat. No. 3,839,796 discloses the use of a hard base and teeth fixed thereto, together with a relatively soft deflectable and formable layer so that the teeth, the hard base and the deflectably formable layer may be inserted in a patient's mouth and wherein the deflectably formable layer may be deflected and form fitted to an edentulus ridge in the patient's mouth whereupon curable plastic material may subsequently be placed in the trough of the soft layer and reinserted in the patient's mouth for final impression fitting such that a hard liner is impression formed adjacent to the soft layer and the resultant denture is as disclosed in said U.S. Pat. No. 3,839,796.

It has however, been desirable to form a totally hard base structure which is impression formed relative to an edentulus ridge in a patient's mouth and various attempts have been made to strip the aforementioned deflectably formable layer from the hard base and cast a final hard impression formed liner against the hard base in dental stone molds. This has been accomplished. However, the stripping of the soft deflectable formable layer from the hard base preliminary to casting the final layer in dental stone molds has been difficult and, in many instances, the final casting of a curable hard plastic against the base material has resulted in the bonding of said last mentioned plastic to the surfaces of the plastic teeth which are in the dental stone molds and such has caused great difficulty in the cleaning of the final denture and the polishing thereof.

SUMMARY OF THE INVENTION

The present invention comprises a method wherein a plurality of hard base structures are first manufactured in identical form. These hard base structures include a generally U-shaped hard plastic structure with a set of teeth imbedded in and bonded thereto. The hard base structure aforementioned is generally U-shaped and is related to the teachings of U.S. Pat. No. 3,839,796.

The production of a plurality of generally identical U-shaped denture elements comprising a hard base and teeth imbedded therein may be accomplished on a production basis in suitable production molds and the term "identical", as used herein, shall be construed to mean a denture unit or element which is produced in conventional molds by conventional production methods such that the denture units, including the hard base and the prosthetic teeth, are as nearly identical as conventional repeat molding processes can accomplish.

The denture units, including the U-shaped hard base and the teeth, are used in accordance with the present invention first of all to prepare a denture which is impression fitted to a patient in accordance with the teachings of U.S. Pat. No. 3,839,796 whereby an exact model of a denture which fits the patient is first produced in accordance with the teachings of said patent. Said denture including a substantially U-shaped hard base with teeth imbedded therein and a soft deflectable or readily formable layer which is mechanically deflected into conformance with the patient's edentulus ridge and wherein a hard liner is subsequently cast into impression conformance with the edentulus ridge of the patient and such that the final denture includes teeth imbedded in a hard base, a relatively soft layer bonded to the base and a hard liner which is impression formed in accordance with the features of a patient's mouth.

The present method includes the foregoing steps and in addition, the use of one of the aforementioned hard base denture elements of identical form to that used in the aforementioned patient fitted denture. The identical denture element includes the teeth and the U-shaped hard base and is used to procued a final permanent denture as follows:

The aforementioned impression fitted denture, including the hard base, the teeth, the soft deflectable layer and the hard liner cast therein in accordance with the features of the patient's mouth, is used to impression cast a pair of dental stone molds so as to make molds having the impression of the finally fitted denture which has been fitted to the patient's mouth; then this finally fitted denture is removed from the dental stone molds and one of the aforementioned identical denture units, including the U-shaped hard base and the teeth, is placed in one of the cavities of one of the dental stone molds and uncured hard plastic is placed in contiguous relationship with the denture element in opposed relation to the teeth imbedded therein and the remaining member of the set of denture stone molds is closed against the uncured hard plastic, the dental stone molds are enclosed in a flask wherein the last mentioned uncured hard plastic is cured in accordance with the features of the two molds which represent the configuration of the denture fitted impressionably to the aforementioned patient's mouth. The uncured hard plastic is then cured in the molds in the flask by elevating the temperature to a desired degree approximately 200° F for a substantial period of time, whereupon the final denture is removed from the dental stone molds and is polished and finished for installation in the patient's mouth. It will be understood that all of the features are thus transferred to the final denture and that the last mentioned plastic is hard plastic and is bonded to the original hard base structure of the identical denture element which corresponds to that originally used to form the temporary denture which had previously served as a model to produce the dental stone molds.

The method also includes a novel casting shield which is made of elastomeric or rubber-like material. This casting shield is made in production molds and is cast in conformance with exact detail of one of said identical denture elements, which includes the hard U-shaped base aforementioned with the prosthetic teeth cast and bonded therein. The elastomeric or rubber-like casting shield is disposed to surround the outer sides of the teeth and the hard base including the festooned area such as to protect the hard base at the outer sides thereof and the teeth projecting therefrom from the casting of materials adjacent thereto and particularly during the forming of the hereinbefore mentioned dental stone molds as well as the final casting of the permanent artificial denture as aforementioned.

The elastomeric shield is such that it permits portions of the teeth to project therethrough at one side thereof and is open such that the shield exposes the hard U-shaped base so as to permit the casting of hard plastic thereagainst and to bond thereto for the production of the final denture.

In the initial use of the elastomeric shield, it is placed around the temporary denture which includes the aforementioned hard base denture element, including the hard base structure with the teeth therein. Also, the deflectably formable layer and the hard liner as impression fitted to the patient's mouth. At this point, the elastomeric casting shield is placed around the outer portions of the teeth and has been previously cast to fit identically in geometry around the teeth of the temporary denture and the temporary denture is then inserted in a position wherein it is cast in a pair of opposed dental stone molds with the elastomeric casting shield surrounding the teeth and preventing the dental stone from being cast against and adhering to the outer sides of the teeth, and thus leaving one cavity of the dental stone mold which is cast around the temporary denture so formed to accept the elastomeric casting shield when it is subsequently placed therein around another one of the identical denture elements hereinbefore referred to. Thus, when the final denture is being produced, one of the identical denture elements including teeth and U-shaped hard base is surrounded and contained within the elastomeric casting shield and this, together with the casting shield, is placed in the aforementioned mold which was cast in accordance with the temporary patient fitted denture and the elastomeric shield fits in the same cavity previously formed in the mold by the elastomeric shield on the temporary denture. Thus, the second denture element surrounded by the elastomeric shield is in one of the molds and the final uncured hard plastic material is then cast against the denture element in opposed relationship with the teeth thereof, and the teeth project slightly from the one side of the shield to establish an exact location of the teeth in the dental stone mold. The curable hard plastic is then molded and bonded to the identical U-shaped hard base in accordance with the features of the mold which were cast against the temporary patient fitted denture.

At this time, when the pressure is applied in the flask against the dental stone mold, the uncured hard plastic is forced into intimate geometrical contact with all features of the mold which were produced in accordance with the patient fitted temporary denture. At this time, the permanent denture is formed without the soft deflectable formable layer but includes only a hard base with a hard upper portion which contains all the exact geometry to fit the edentulus ridge of a patient's mouth which was impression fitted by the temporary denture produced in accordance with U.S. Pat. No. 3,839,796.

Accordingly, the final denture produced in accordance with the present invention is such that it includes a hard base with teeth projecting therefrom and a hard edentulus fitting area bonded to the hard base so that all of the structure of the permanent or final denture is hard material without any relatively soft deflectable layer portions therein.

The aforementioned identical denture element, including the U-shaped hard base and teeth, is designed initially to serve as a flat plane occlusion type denture when in the final denture hereinbefore described and therefore the teeth projecting from the hard U-shaped base are finished in a geometrical arrangement whereby they provide flat plane occlusion and result in the production of a final denture which is compatible with the fitting of such denture to patient's such that they have efficient occlusion and such that great versatility is provided in the production and fitting of artificial dentures to patients in order that they may have occlusion and mastication service therefrom.

Thus, each identical denture element hereinbefore referred to preferably contains the geometric features commonly known as flat plane occlusion geometry.

Accordingly, it is an object of the present invention to provide a method for producing artificial dentures wherein the volume production of identical denture units and casting shields permits a dentist substantial facility in the production of custom dentures which custom fit the mouths of patients.

Another object of the invention is to provide a very simple and economical method for producing custom dentures having hard plastic material, such as acrylic material or the like, throughout whereby a high quality custom denture may be quickly and accurately produced with a minimum of time and expense.

Another object of the invention is to provide a novel elastomeric shield for use in shielding a denture unit comprising prosthetic teeth and a U-shaped hard base while initially casting dental stone molds from a temporary denture and doing the final casting of the permanent denture in dental molds and within the usual dental flasks.

Another object of the invention is to provide a method which extends and simplifies the use of the teachings of U.S. Pat. No. 3,839,796 for the production of custom dentures which have hard plastic structures throughout.

Another object of the invention is to provide a method wherein identical hard base denture units, as well as elastomeric shields are produced in identical conformance with each other and in production plurality so as to provide very simple means by which a dentist may preliminarily provide a temporary denture having all the geometrical features of a patient's mouth and whereby that temporary denture may be used to set up dental stone molds to produce a very accurate permanent denture having hard plastic materials throughout.

Further objects and advantages of the invention may be apparent from the following specification, appended claims and accompanying drawings.

BRIEF DESCRIPTION OF THE DRAWINGS

FIG. 7 is a view similar to FIG. 6 with the upper dental stone mold removed from the flask and showing an identical denture element in the lower one of the dental stone molds preliminary to the casting of the final or permanent denture; and FIG. 8 is a view similar to FIGS. 6 and 7 but showing the casting of a final permanent denture in molds produced from the temporary denture shown in FIG. 6 of the drawings.

DESCRIPTION OF THE PREFERRED EMBODIMENTS

Figure 1:
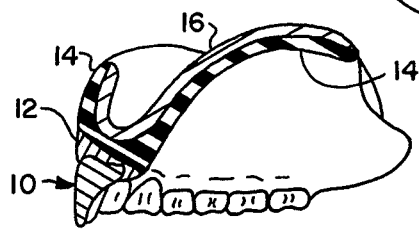
FIG. 1 is a sectional view of an artificial denture produced in accordance with the teachings of U.S. Pat. No. 3,839,796 and showing a hard base with artificial teeth having a soft layer bonded thereto; this layer being a deflectably formable layer and a hard liner inside the deflectably formable layer which has been impression fitted to the edentulus ridges of a patient's mouth.

In accordance with the method of the invention, a temporary artificial denture is produced as shown in FIG. 1 of the drawings and in accordance with the teachings of U.S. Pat. No. 3,839,796. The temporary denture includes artificial teeth 10 cast in a hard base 12 on which a soft deflectable layer 14 is secured; the layer 14 being deflectably formed into engagement with an edentulus ridge of a patient's mouth and thereafter removed so as to permit the placement of uncured hard plastic material therein, ultimately to form an impression formed hard liner 16. Thus, the hard liner 16 contains the exact impression of the patient's edentulus ridge and is cured so as to provide a very accurate fitting of the temporary artificial denture shown in FIG. 1 in accordance with the present invention.

This temporary denture, or course, includes the soft layer 14 and which is absent from the permanent or final denture as indicated at 18 in FIG. 8 of the drawings, all as will be hereinafter described in detail.

Figure 2:
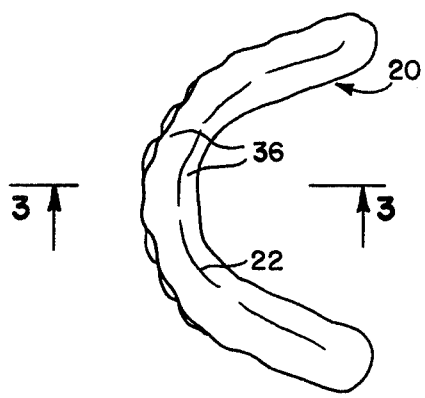
FIG. 2 is a top or plan view of an artificial denture unit in accordance with the present invention.
Figure 3:
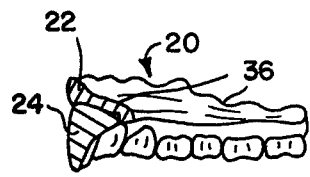
FIG. 3 is a sectional view taken from the line 3—3 of FIG. 2.

In accordance with the present invention, the hard base 12 and teeth 10 are produced as shown in FIGS. 2 and 3 of the drawings in volume production and pluralities of such artificial denture units are produced in identical form so as to be used in accordance with the method of the invention, as will be hereinafter described in detail.

Each artificial denture unit is generally designated 20 in FIGS. 2 and 3 of the drawings. Each artificial denture unit 20 comprises a hard base 22 and a plurality of prosthetic teeth 24 cast in and bonded to the hard base 22. Both the prosthetic teeth 24 and the hard base 22 are hard durable material, such as an acrylic or the like, and are generally U-shaped as shown in FIG. 2 of the drawings. The term identical as used herein is intended to mean that each denture unit 20 is produced in production molds, which are precision molds and all are as identically accurate to each other as such tooling can produce.

Figure 4:
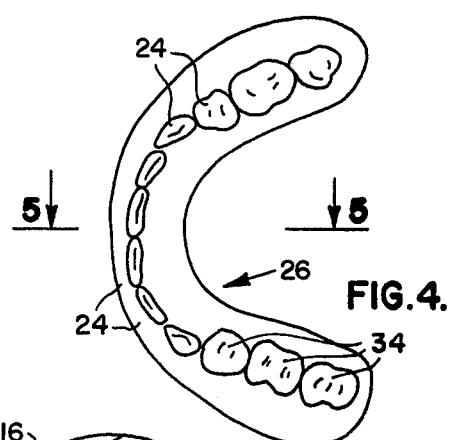
FIG. 4 is a view taken from the line 4—4 of FIG. 3 showing an elastomeric casting shield placed around the sides of the artificial denture unit shown in FIG. 3.
Figure 5:
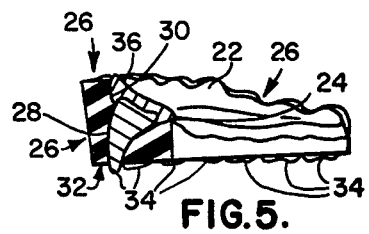
FIG. 5 is a sectional view taken from the line 5—5 of FIG. 4.

Further, in accordance with the invention, an elastomeric casting shield generally designated 26 is produced in volume from precision molds. This shield 26 is substantially as shown in FIGS. 4 and 5 of the drawings and precisely fits the outer surfaces of the teeth 24 and the U-shaped hard base 22, shown in FIGS. 2 and 3 of the drawings. These two separate high production items, namely the denture unit 20 and the casting shield 26, are available in matched sets. Thus, the elastomeric casting shield is available to fit a particular size denture unit 20 and adapted intimately to fit all of the geometrical features of the teeth 24 at their outer surfaces 28 and also to fit the outer surface 30 of the hard base 22 of the denture unit shown in FIGS. 2 and 3 of the drawings. The casting shield 26 is of elastomeric material and may be readily stretched into position and into intimately fitted relation with the denture units 20, all as will be hereinafter described.

The structure of each casting shield 26 includes a normally lower edge 32 through which occluding portions 34 of the artificial teeth 24 extend. Additionally, each casting shield 26 is open at its normally upper portion so as to expose an upper surface area 36 of the hard base 22 so as to permit the casting of an additional upper hard base structure into bonded relation therewith, as will be hereinafter described in detail. This surface 36 is opposite to the occlusion portions 34 of the teeth 24, all as shown best in FIGS. 4 and 5 of the drawings.

Figure 6:
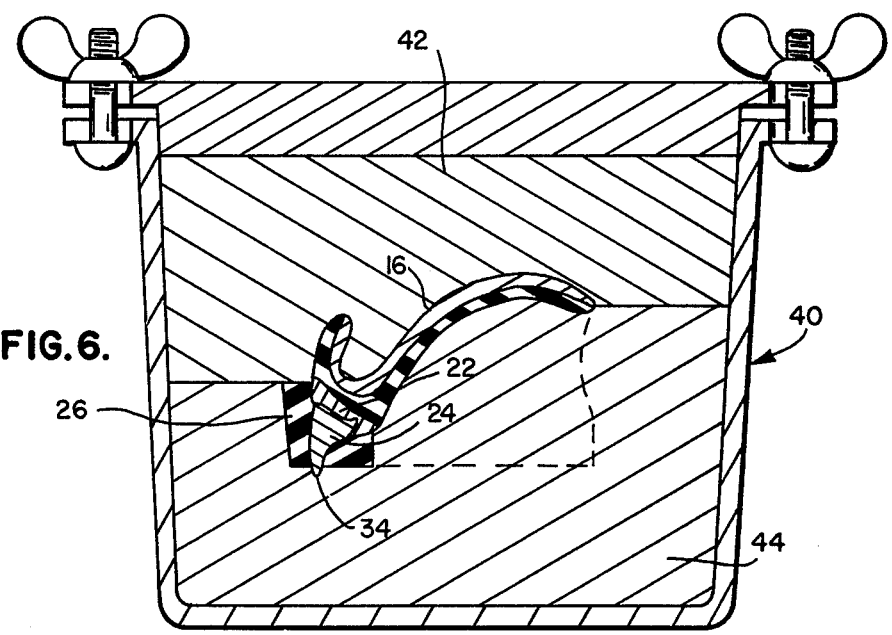
FIG. 6 is a sectional view of the temporary denture shown in FIG. 1 with the casting shield shown in FIGS. 4 and 5 placed thereon and showing the artificial temporary denture and the casting shield in a dental flask with a pair of dental stone molds cast around the temporary denture and around the casting shield.

As shown in FIG. 6 of the drawings, the temporary denture disclosed in FIG. 1, including the teeth 10, the hard base 12, the soft layer 14, and the hard liner 16, is placed in position in a conventional dental flask 40 so as to produce dental stone molds 42 and 44. The dental stone mold 44 is cast around the casting shield 26 which is positioned over the prosthetic teeth 24 at their outer sides and in surrounding relation with the hard base 22 and such that the occlusion areas 34 of the prosthetic teeth 24 are projected slightly into the dental stone mold 44 so as to attain precise location therein. The casting of the mold 44 is such that the elastomeric shield 26 protects the teeth 24 and the hard base 22 from being contacted by the dental stone 44 and prevents the dental stone 44 from adhering to substantial areas of the teeth 24 and the hard base 22. The hard liner 16 of the temporary denture shown in the molds in FIG. 6 provides a surface which offers a reference to the exact geometry of the edentulus ridge to which it was previously fitted so that the molds 42 and 44 are produced to contain all of the geometry of the desired final or permanent denture which is disclosed in FIG. 8 and will be hereinafter described in detail.

As shown in FIG. 7, the temporary denture, as illustrated in FIG. 1, has been removed from the mold 44 and the mold 42 has been removed from the flask 40 and another one of the identical denture elements 20 has been inserted into the casting shield 26 or a new identical casting shield 26 may be placed in the mold 44. Thus, the casting shield 26 is then located in the mold in surrounding relation to the new identical denture element which is identical to the one shown in FIG. 1 and identical to the one forming a part of the temporary denture shown in the mold in FIG. 6 of the drawings and therefore the identical denture unit of the temporary denture is removed and another identical denture element 20 is inserted in the mold 44 with the shield 26 therearound, as shown in FIG. 7. At this time, plastic material, such as an acrylic material is placed in an uncured form in contact with the upper surface 36 of the hard base 22 which is opposite to the occlusion portions 34 of the artificial teeth 24 of the identical denture unit. The occlusion portions 34 fit into the recesses cast around the previous identical unit in the mold 44, thereby precisely locating the denture unit 20 in the mold 44 and the shield 26 surrounds the inner and outer sides of the teeth 24 and the hard base 22 and the shield being open at the top exposes the upper portion 36 of the hard base, which is opposite to the teeth 24.

When the hard plastic material 18 is placed on the surface 36 of the hard base 22, it is in soft uncured condition and the mold 42 is placed thereover in the flask 40 and the flask 40 is then closed with its conventional cover and tightened to press the mold 42 toward the mold 44 and to thereby set up the hard plastic material 18 so that it may be cured by pressure and heat in the flask 40 and molds 42 and 44.

It will be understood that the mold structures 42 and 44 contain the exact geomertrical detail of the previously patient fitted temporary denture, shown in FIGS. 1 and 6 of the drawings.

During the process of pressurizing the uncured material 18 in the molds 42 and 44, the elastomeric shield or casting shield 26 shields the outer and inner portions of the prosthetic teeth 24 and the hard base 22 from the flow of the uncured resin 18 so as to prevent this resin from bonding onto the outer surfaces of the teeth 24 and the hard base 22. Thus, the shield 26 being resilient intimately fits these outer surfaces and thereby eliminates the usual hard work of removing dental stone and/or plastic material from the teeth after the final casting operation has been accomplished.

After the hard plastic material 18 has been cured, it is then intimately bonded to and integral with the upper portion 36 of the hard base 22 and the final or permanent denture, such as shown in FIG. 8, is removed from the dental stone molds 42 and 44 after they have been removed from the flask 40 and the casting shield 26, being resilient, is readily and easily deflected from its position around the teeth 24 and hard base 22 and the final denture or permanent denture is merely cleaned and polished and is then completely ready to take a permanent fitted position in the patient's mouth in accordance with exact geometry established in the impression fitting of a temporary denture shown in FIGS. 1 and 6 of the drawings.

It will be obvious to those skilled in the art that various modifications may be resorted to without departing from the spirit of the invention.

I claim:

1. A method for producing artificial dentures comprising: preparing a plurality of substantially identical generally U-shaped hard base denture elements; each hard base element having a substantially identical set of teeth fixed therein; securing a formable edentulus ridge fitting layer onto one of said hard base denture elements; then formably fitting said ridge fitting layer to an edentulus ridge in a human patient's mouth; then removing said denture element with the so formed layer and placing curable impression formable material in said layer and reinserting said layer and denture element in the patient's mouth to impression fit said impression formable material to said edentulus ridge and allowing said curable material to cure in fixed position; then placing a rubber-like shield around said teeth and said denture element; then impression forming a pair of denture stone molds on said denture element, said teeth, said shield, said layer and said cured curable material; placing one of said dental stone molds in a flask; placing said shield around the side of another one of said identical denture elements and placing said last mentioned dental element and said shield in said one of said dental stone molds; placing curable plastic material adjacent said last mentioned one of said denture elements contiguous with a surface thereof opposite to said teeth; closing the other one of said molds over said last mentioned curable plastic material; closing said flask over said molds and allowing said last mentioned curable plastic material to cure, harden and bond to said last mentioned identical denture elements in said mold to thereby form an artificial denture that fits said edentulus ridge.

2. The invention as defined in claim 1, wherein: said shield is cast of an elastomeric material and wherein and occlusal surfaces of said teeth and opposite surfaces of said denture element project through said shield to serve in the impression forming of the respective mold thereby; and wherein the surface of said denture element which is disposed in opposed relation to said teeth is not covered by said shield so as to permit said last mentioned curable plastic to bond thereto when in said molds and when said molds are enclosed in said flask.

3. A method for producing artificial dentures comprising: preparing a plurality of substantially identical generally U-shaped hard base denture elements; each hard base element having a substantially identical set of teeth fixed therein; providing said set of teeth with flat plane occlusion geometry; securing a formable edentulus ridge fitting layer onto one of said hard base denture elements; then formably fitting said ridge fitting layer to an edentulus ridge in a human patient's mouth; then removing said denture element with the so formed layer and placing curable impression formable material in said layer and reinserting said layer and denture element in the patient's mouth to impression fit said impression formable material to said edentulus ridge and allowing said curable material to cure in fixed position on said layer; placing a rubber-like shield around the sides of said teeth and said denture element; impression forming a pair of dental stone molds on said denture element, said teeth, said shield, said layer and said cured curable material; then placing one of said dental stone molds in a flask and placing said shield around the side of another one of said identical denture elements and placing said last mentioned dental element and said shield in said one of said dental stone molds; then placing curable plastic material adjacent said last mentioned one of said denture elements contiguous with a surface thereof opposite the set teeth; closing the other one of said molds over said last mentioned curable plastic material; closing said flask over said mold and allowing said last mentioned curable plastic material to cure, harden and bond to said last mentioned identical denture element in said molds to thereby form an artificial denture that fits said edentulus ridge.

* * * * *